United States Patent
Perschbacher et al.

(10) Patent No.: US 10,744,334 B2
(45) Date of Patent: Aug. 18, 2020

(54) SYSTEMS AND METHODS FOR ARRHYTHMIA DETECTION

(71) Applicant: Cardiac Pacemakers, Inc., St. Paul, MN (US)

(72) Inventors: David L. Perschbacher, Coon Rapids, MN (US); Arjun D. Sharma, St. Paul, MN (US); Sunipa Saha, Shoreview, MN (US); Krzysztof Z. Siejko, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 266 days.

(21) Appl. No.: 15/786,824

(22) Filed: Oct. 18, 2017

(65) Prior Publication Data
US 2018/0104502 A1    Apr. 19, 2018

Related U.S. Application Data

(60) Provisional application No. 62/409,515, filed on Oct. 18, 2016.

(51) Int. Cl.
*A61N 1/39* (2006.01)
*A61B 5/00* (2006.01)
(Continued)

(52) U.S. Cl.
CPC .......... *A61N 1/3925* (2013.01); *A61B 5/046* (2013.01); *A61B 5/7264* (2013.01);
(Continued)

(58) Field of Classification Search
CPC ...... A61N 1/36; A61N 1/3621; A61N 1/3627; A61N 1/3925; A61N 1/395; A61N 1/3956; A61B 5/0452
See application file for complete search history.

(56) References Cited

U.S. PATENT DOCUMENTS 5,755,736 A    5/1998  Gillberg et al.
5,836,975 A *  11/1998 DeGroot ................ A61N 1/056
                                                    607/5
(Continued)

FOREIGN PATENT DOCUMENTS

CN       109843166 A       6/2019
WO       WO-2015168652 A1  11/2015
WO       WO-2018075587 A1  4/2018

OTHER PUBLICATIONS

Dash, S., et al., "A Statistical Approach for Accurate Detection of Atrial Fibrillation and Flutter", Computers in Cardiology; 36:137-140, 2009.
(Continued)

*Primary Examiner* — Christopher A Flory
(74) *Attorney, Agent, or Firm* — Schwegman Lundberg & Woessner, P.A.

(57) ABSTRACT

Systems and methods for detecting cardiac arrhythmias such as an atrial fibrillation (AF) are described herein. The AF detection system includes a sensor circuit to sense a physiological signal, a heartbeat processor to recognize a plurality of beat patterns using cycle length of two more consecutive cardiac cycles. The beat patterns can be indicative of temporal relationship between the consecutive cardiac cycles. The heartbeat processor may generate a repetitiveness indictor based on a statistical measurement of various beat patterns. The AF detection system includes an arrhythmia detector to detect an episode of AF based on the repetitiveness indictor, and to discriminate the AF from other arrhythmias of atrio-ventricular conduction abnormalities.

20 Claims, 6 Drawing Sheets

(51) Int. Cl.
*A61B 5/046* (2006.01)
*A61N 1/362* (2006.01)
*A61B 5/0452* (2006.01)

(52) U.S. Cl.
CPC ......... *A61N 1/3627* (2013.01); *A61N 1/3956* (2013.01); *A61B 5/0452* (2013.01); *A61N 1/3621* (2013.01)

(56) References Cited

U.S. PATENT DOCUMENTS

| | | | | |
|---|---|---|---|---|
| 5,865,838 | A * | 2/1999 | Obel | A61N 1/3621 607/14 |
| 5,987,356 | A * | 11/1999 | DeGroot | A61N 1/3622 607/5 |
| 6,081,746 | A * | 6/2000 | Pendekanti | A61N 1/3622 607/5 |
| 6,085,116 | A * | 7/2000 | Pendekanti | A61N 1/3622 607/5 |
| 6,285,907 | B1 * | 9/2001 | Kramer | A61N 1/3621 607/25 |
| 6,292,691 | B1 * | 9/2001 | Pendekanti | A61N 1/3962 607/14 |
| 6,327,499 | B1 * | 12/2001 | Alt | A61N 1/36542 607/4 |
| 6,754,525 | B1 * | 6/2004 | Province | A61N 1/3925 607/4 |
| 2001/0016759 | A1 * | 8/2001 | Kramer | A61N 1/3621 607/9 |
| 2003/0004551 | A1 * | 1/2003 | Chen | A61N 1/3621 607/14 |
| 2003/0055351 | A1 * | 3/2003 | Wiesel | A61B 5/046 600/515 |
| 2003/0216654 | A1 * | 11/2003 | Xu | A61B 5/0452 600/509 |
| 2004/0077941 | A1 * | 4/2004 | Reddy | A61B 6/032 600/428 |
| 2006/0195037 | A1 * | 8/2006 | Wiesel | A61B 5/024 600/518 |
| 2006/0247547 | A1 * | 11/2006 | Sarkar | A61B 5/0464 600/515 |
| 2006/0247548 | A1 * | 11/2006 | Sarkar | A61B 5/046 600/515 |
| 2008/0281368 | A1 * | 11/2008 | Bulkes | A61N 1/36114 607/4 |
| 2009/0012412 | A1 * | 1/2009 | Wiesel | A61B 5/024 600/508 |
| 2009/0076563 | A1 * | 3/2009 | Krig | A61N 1/3622 607/17 |
| 2009/0204164 | A1 * | 8/2009 | Efimov | A61N 1/3956 607/17 |
| 2011/0009916 | A1 * | 1/2011 | Efimov | A61N 1/3956 607/5 |
| 2011/0137193 | A1 * | 6/2011 | Ghanem | A61B 5/02405 600/515 |
| 2011/0152957 | A1 | 6/2011 | Shaquer | |
| 2012/0101541 | A1 * | 4/2012 | Corbucci | A61B 5/0468 607/17 |
| 2013/0144146 | A1 * | 6/2013 | Linker | A61B 5/0031 600/393 |
| 2014/0052013 | A1 * | 2/2014 | Narayan | A61B 5/046 600/518 |
| 2014/0114204 | A1 * | 4/2014 | Narayan | A61B 5/0422 600/518 |
| 2014/0142443 | A1 * | 5/2014 | Ngo | A61B 5/0006 600/486 |
| 2014/0228696 | A1 * | 8/2014 | Narayan | A61B 5/046 600/518 |
| 2014/0371616 | A1 * | 12/2014 | Narayan | A61B 5/046 600/518 |
| 2015/0005653 | A1 * | 1/2015 | Michaelis | A61B 5/02438 600/519 |
| 2015/0051452 | A1 * | 2/2015 | Ciaccio | A61B 5/7257 600/301 |
| 2015/0141860 | A1 * | 5/2015 | Linker | A61B 5/0031 600/516 |
| 2015/0216438 | A1 * | 8/2015 | Bokan | A61B 5/4836 600/515 |
| 2015/0223711 | A1 | 8/2015 | Raeder et al. | |
| 2016/0089048 | A1 * | 3/2016 | Brodnick | A61B 5/7246 600/512 |
| 2016/0220139 | A1 | 8/2016 | Mahajan et al. | |
| 2016/0249823 | A1 * | 9/2016 | Galloway | A61B 5/7203 600/518 |
| 2016/0262643 | A1 * | 9/2016 | Ng | A61B 5/7246 |
| 2016/0287115 | A1 | 10/2016 | Perschbacher et al. | |
| 2017/0367601 | A1 * | 12/2017 | Bars | A61B 5/04012 |
| 2018/0310892 | A1 * | 11/2018 | Perschbacher | A61B 5/746 |
| 2019/0223739 | A1 * | 7/2019 | Rapin | A61B 5/04012 |
| 2019/0232067 | A1 * | 8/2019 | Mahajan | A61B 5/046 |

OTHER PUBLICATIONS

Dash, S., et al., "Automatic Real Time Detection of Atrial Fibrillation", Annals of Biomedical Engineering (2009) 9 pages.
"International Application Serial No. PCT/US2017/057100, International Preliminary Report on Patentability dated May 2, 2019", 7 pgs.
"International Application Serial No. PCT/US2017/057100, International Search Report dated Jan. 25, 2018", 4 pgs.
"International Application Serial No. PCT/US2017/057100, Written Opinion dated Jan. 25, 2018", 5 pgs.

* cited by examiner

SYSTEMS AND METHODS FOR ARRHYTHMIA DETECTION

CLAIM OF PRIORITY

This application claims the benefit of priority under 35 U.S.C. § 119(e) of U.S. Provisional Patent Application Ser. No. 62/409,515, filed on Oct. 18, 2016, which is herein incorporated by reference in its entirety.

TECHNICAL FIELD

This document relates generally to medical devices, and more particularly, to systems, devices and methods for detecting and managing cardiac arrhythmias.

BACKGROUND

Implantable medical devices (IMDs) have been used for monitoring patient health condition or disease states and delivering therapies. For example, implantable cardioverter-defibrillators (ICDs) may be used to monitor for certain abnormal heart rhythms and to deliver electrical energy to the heart to correct the abnormal rhythms. Some IMDs may be used to monitor for chronic worsening of cardiac hemodynamic performance, such as due to congestive heart failure (CHF), and to provide cardiac stimulation therapies, including cardiac resynchronization therapy (CRT) to correct cardiac dyssynchrony within a ventricle or between ventricles.

Some IMDs are capable of detecting cardiac arrhythmias, such as atrial fibrillation (AF). AF is the most common clinical arrhythmia affecting millions of people. During AF, disorganized electrical pulses originated from regions in or near an atrium may lead to irregular conductions to ventricles, thereby causing inappropriately fast and irregular heart rate. AF may be paroxysmal that may last from minutes to days before it stops by itself, persistent that may last for over a week and typically requires medication or other treatment to revert to normal sinus rhythm, or permanent where a normal heart rhythm cannot be restored with treatment. Timely detection of AF may be clinically important for assessing progression of AF.

OVERVIEW

Implantable medical devices are capable of detecting physiological events, such as cardiac arrhythmias or progression of chronic heart diseases, and obtaining sampled values of cardiac electrical activity signals such as electrograms. Some IMDs may further be communicated with multiple physiological sensors that may measure various physiological signals. The IMD may be programmed to monitor and store data sensed from some or all of the physiological sensors.

Capturing accurate electrogram or other physiological sensor information obtained over a longer period of time, such as chronically between regularly-scheduled outpatient office visits, may help the physician re-program the device, if needed, or to diagnose and assess the patient's condition. In an IMD programmed to detect cardiac arrhythmias such as atrial fibrillation (AF) episodes, noise, motion artifacts, or cardiac rhythms other than the AF episode may be inappropriately detected as AF episodes. Inappropriate arrhythmia detection may reduce detection specificity and result in inappropriate AF therapy. Alerts to clinicians of inappropriately detected arrhythmic events, or presenting to clinicians a large volume of inappropriately detected arrhythmic events for review or adjudication, may adversely affect the device efficacy and unwarrantedly increase the cost associated with patient management. For at least these reasons, the present inventors have recognized, among other things, substantial challenges and a demand for a more efficient arrhythmic detection and reporting system.

This document discusses, among other things, systems, devices, and methods for detecting cardiac arrhythmias such as AF. An AF detection system may include a sensor circuit to sense a physiological signal and a heartbeat processor to recognize various beat patterns based on cycle lengths of two more consecutive cardiac cycles. The beat patterns each represents temporal relationship between consecutive cardiac cycles. The heartbeat processor may generate a repetitiveness indictor based on a statistical measurement of various beat patterns. The AF detection system includes an arrhythmia detector that may detect AF based on the repetitiveness indictor, and to discriminate AF from other arrhythmias with atrio-ventricular conduction abnormalities.

Example 1 is a system for detecting cardiac arrhythmia. The system may comprise: a sensor circuit configured to sense a physiological signal, a heartbeat processor, and an arrhythmia detector coupled to the heartbeat processor. The heartbeat process may be configured to determine cardiac cycle lengths (CLs) from the sensed physiological signal; recognize a plurality of beat patterns based on respective two or more consecutive CLs, where the beat pattern indicates a temporal relationship between the two or more consecutive cardiac cycles; and generate a repetitiveness indicator of the beat pattern based on a statistical measurement of the plurality of beat patterns, where the repetitiveness indicator indicates randomness of the CLs. The arrhythmia detector may be configured to detect atrial fibrillation (AF) based on the repetitiveness indicator of the beat pattern.

In Example 2, the subject matter of Example 1 optionally includes a therapy circuit configured to generate and deliver an AF therapy in response to the detection of the AF.

In Example 3, the subject matter of any one or more of Examples 1-2 optionally include the beat pattern that may include a cycle length statistic of consecutive cardiac cycles, and the repetitiveness indicator includes a count of the computed cycle length statistics that are substantially identical within a specified tolerance. The arrhythmia detector is configured to detect the AF when the count of the computed cycle length statistics falls below an AF threshold.

In Example 4, the subject matter of Example 3 optionally includes the cycle length statistic that may include one of a maximum cycle length, a minimum cycle length, or a median cycle length each computed from the consecutive cardiac cycles within a time window.

In Example 5, the subject matter of any one or more of Examples 3-4 optionally include the count of the computed cycle length statistics that may include a relative count, and the arrhythmia detector is configured to detect the AF when the computed count of the computed cycle length statistics exceeds a threshold value of at least 50%.

In Example 6, the subject matter of any one or more of Examples 3-5 optionally include the cycle length statistic that is computed from consecutive cardiac cycles within a time window having a specified time duration or specified number of cardiac cycles.

In Example 7, the subject matter of any one or more of Examples 1-6 optionally include the beat patterns that may include an ascending CL sequence of two or more consecutive cardiac cycles progressively increasing by at least a specified step size, and a descending CL sequence of two or more consecutive cardiac cycles progressively decreasing by at least a specified step size; wherein the heartbeat processor is configured to determine the repetitiveness indicator using a first count of ascending CL sequences and a second count of descending CL sequences from the determined cardiac cycles; and wherein the arrhythmia detector is configured to detect the AF when the generated repetitiveness indicator falls below an AF threshold.

In Example 8, the subject matter of Example 7 optionally includes the beat patterns that further includes an identical CL sequence of two or more consecutive cardiac cycles of substantially identical CL. The heartbeat processor is configured to generate the repetitiveness indicator further using a third count of identical CL sequences.

In Example 9, the subject matter of any one or more of Examples 7-8 optionally include the heartbeat processor that may be configured to generate the repetitiveness indicator using (1) an accumulative observed count including the first count of ascending CL sequences and the second count of descending CL sequences, (2) an expected count computed using the first and second counts, and (3) a standard deviation of counts of the ascending and descending CL sequences.

In Example 10, the subject matter of any one or more of Examples 1-9 optionally include the arrhythmia detector further configured to detect atrioventricular conduction abnormality (ACA) when the repetitiveness indicator exceeds an ACA threshold.

In Example 11, the subject matter of Example 10 optionally includes the atrioventricular conduction abnormality includes Wenckebach rhythm.

In Example 12, the subject matter of any one or more of Examples 1-11 optionally include an ambulatory device that may include at least a portion of one or more of the sensor circuit, the heartbeat processor, or the arrhythmia detector.

In Example 13, the subject matter of Example 12 optionally includes the ambulatory device that may include an implantable or wearable device.

In Example 14, the subject matter of any one or more of Examples 1-13 optionally include the heartbeat processor that is further configured to compute a stability of the CLs; and the arrhythmia detector is configured to detect the AF further based on the stability of the CLs and the repetitiveness indicator of the beat pattern.

In Example 15, the subject matter of Example 14 optionally includes the stability of the CLs includes a CL distribution according to a histogram of the CLs.

Example 16 is a method for detecting cardiac arrhythmia. The method comprises sensing a physiological signal; determining cardiac cycle lengths (CLs) from the sensed physiological signal; recognizing a plurality of beat patterns using respective two or more consecutive CLs, the beat pattern indicating a temporal relationship between the two or more consecutive cardiac cycles; generating a repetitiveness indicator of the beat pattern based on a statistical measurement of the plurality of beat patterns, the repetitiveness indicator indicating randomness of the determined CLs; and detecting atrial fibrillation (AF) based on the repetitiveness indicator of the beat pattern.

In Example 17, the subject matter of Example 16 optionally includes generating and delivering an AF therapy in response to the detection of AF.

In Example 18, the subject matter of any one or more of Examples 16-17 optionally include the beat pattern that may include a cycle length statistic of consecutive CLs; and the repetitiveness indicator includes a count of the computed cycle length statistics that are substantially identical within a specified tolerance; wherein the detection of AF includes detecting AF when the count of the computed cycle length statistics falls below an AF threshold.

In Example 19, the subject matter of Example 18 optionally includes wherein the cycle length statistic includes one of a maximum cycle length, a minimum cycle length, or a median cycle length each computed from the consecutive CLs within a time window.

In Example 20, the subject matter of any one or more of Examples 16-19 optionally include the beat patterns that may include an ascending CL sequence of two or more consecutive cardiac cycles progressively increasing by at least a specified step size, and a descending CL sequence of two or more consecutive cardiac cycles progressively decreasing by at least a specified step size. The repetitiveness indicator may be generated using a first count of ascending CL sequences and a second count of descending CL sequences from the determined cardiac cycles; and detecting AF includes detecting AF when the generated repetitiveness indicator falls below an AF threshold.

In Example 21, the subject matter of Example 20 optionally includes the beat patterns that may further include an identical CL sequence of two or more consecutive cardiac cycles of substantially identical CL, and wherein determining the repetitiveness indicator further includes using a third count of identical CL sequences.

In Example 22, the subject matter of any one or more of Examples 16-21 optionally include detecting an atrioventricular conduction abnormality (ACA) when the repetitiveness indicator exceeds an ACA threshold.

In Example 23, the subject matter of any one or more of Examples 16-22 optionally include computing a stability of the CLs, wherein the detection of AF further includes detecting AF based on the stability of the CLs and the repetitiveness indicator of the beat pattern.

In Example 24, a system may optionally combine any portion or combination of any portion of any one or more of Examples 1-23 to include "means for" performing any portion of any one or more of the functions or methods of Examples 1-23, or a "non-transitory machine-readable medium" including instructions that, when performed by a machine, cause the machine to perform any portion of any one or more of the functions or methods of Examples 1-23.

Although the discussion herein focuses on cardiac arrhythmia detection, this is meant only by way of example and not limitation. The systems, devices, and methods discussed in this document, such as the beat patterns and repetitiveness indicator indicating a degree of organization of the rhythm, may also be used for monitoring physiologic events other than cardiac arrhythmias, including progression of a chronic disease, such as a worsening heart failure, heart failure decompensation, pulmonary edema, pulmonary condition exacerbation, asthma and pneumonia, myocardial infarction, dilated cardiomyopathy, ischemic cardiomyopathy, valvular disease, renal disease, chronic obstructive pulmonary disease, peripheral vascular disease, cerebrovascular disease, hepatic disease, diabetes, anemia, or depression, among others.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting cardiac arrhythmias such as an atrial fibrillation (AF). The AF detection system includes a sensor circuit to sense a physiological signal, a heartbeat processor to recognize beat patterns using cycle length of two more consecutive cardiac cycles. The beat pattern can be indicative of temporal relationship between the consecutive cardiac cycles. The heartbeat processor may generate a repetitiveness indictor based on a statistical measurement of various beat patterns. The AF detection system includes an arrhythmia detector to detect AF based on the repetitiveness indictor, and to discriminate AF from other arrhythmias with atrio-ventricular conduction abnormalities.

Figure 1:
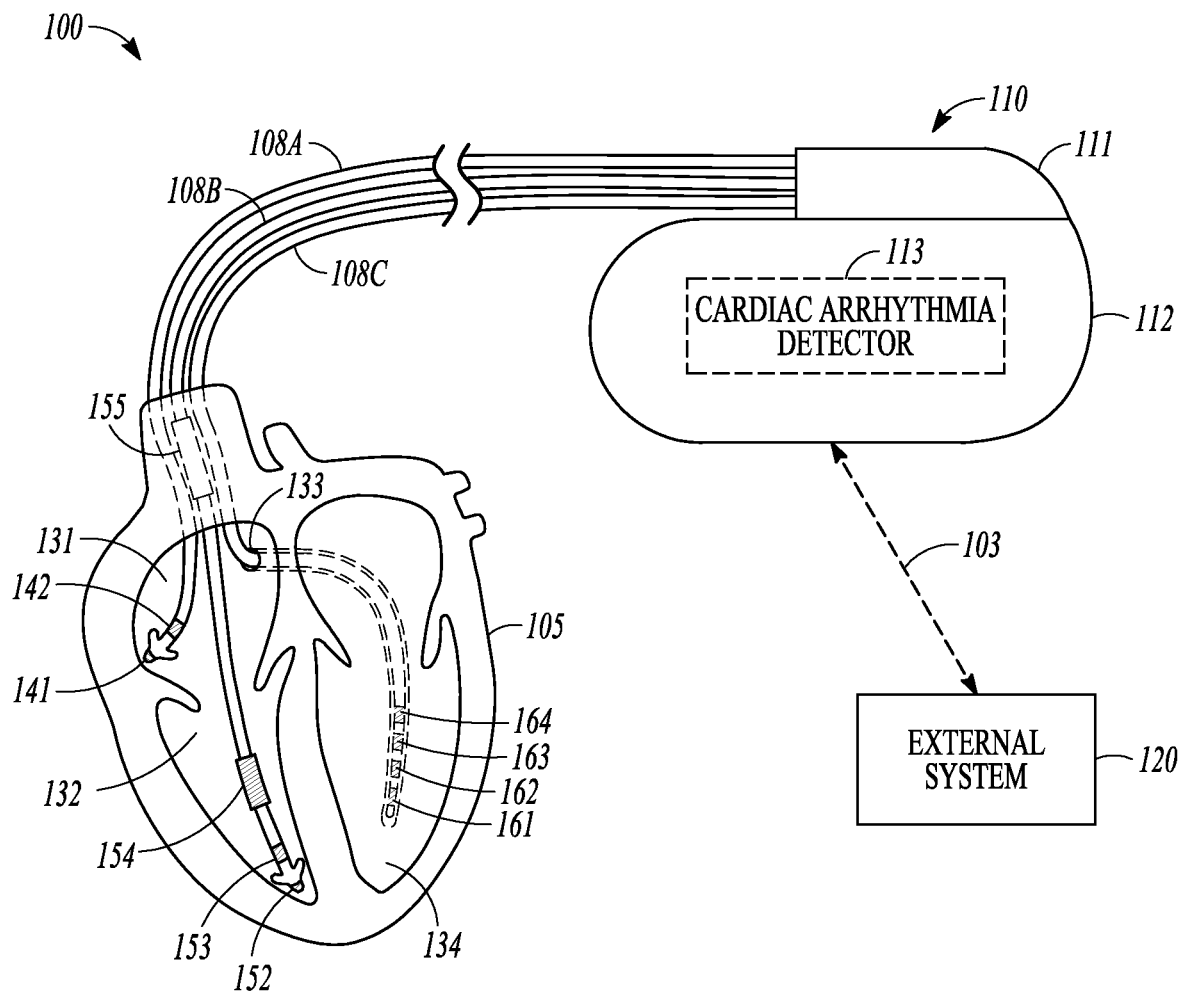
FIG. 1 illustrates an example of a Cardiac Rhythm Management (CRM) system and portions of an environment in which the CRM system may operate.

FIG. 1 illustrates generally an example of a Cardiac Rhythm Management (CRM) system 100 and portions of an environment in which the CRM system 100 may operate. The CRM system 100 may include an ambulatory medical device, such as an implantable medical device (IMD) 110 that may be electrically coupled to a heart 105 such as through one or more leads 108A-C, and an external system 120 that may communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). In some examples, the CRM system may include one or more monitoring or therapeutic devices such as a subcutaneously implanted device, a neural stimulator, a drug delivery device, a biological therapy device, an ambulatory medical device, or a wearable external device such as a smartphone, a smartwatch, a wearable fitness or activity tracker, or a wearable health monitor. The IMB 110 may be coupled to, or may be substituted by a monitoring medical device such as a bedside or other external monitor.

The IMB 110 may include a hermetically sealed can housing 112 that may house an electronic circuit that may sense a physiological signal in the heart 105 and may deliver one or more therapeutic electrical pulses to a target region, such as in the heart, such as through one or more leads 108A-C. The CRM system 100 may include only one lead such as 108B, or may include two leads such as 108A and 108B.

The lead 108A may include a proximal end that may be configured to be connected to IMB 110 and a distal end that may be configured to be placed at a target location such as in the right atrium (RA) 131 of the heart 105. The lead 108A may have a first pacing-sensing electrode 141 that may be located at or near its distal end, and a second pacing-sensing electrode 142 that may be located at or near the electrode 141. The electrodes 141 and 142 may be electrically connected to the IMD 110 such as via separate conductors in the lead 108A, such as to allow for sensing of the right atrial activity and optional delivery of atrial pacing pulses. The lead 108B may be a defibrillation lead that may include a proximal end that may be connected to IMB 110 and a distal end that may be placed at a target location such as in the right ventricle (RV) 132 of heart 105. The lead 108B may have a first pacing-sensing electrode 152 that may be located at distal end, a second pacing-sensing electrode 153 that may be located near the electrode 152, a first defibrillation coil electrode 154 that may be located near the electrode 153, and a second defibrillation coil electrode 155 that may be located at a distance from the distal end such as for superior vena cava (SVC) placement. The electrodes 152 through 155 may be electrically connected to the IMD 110 such as via separate conductors in the lead 108B. The electrodes 152 and 153 may allow for sensing of a ventricular electrogram and may allow delivery of one or more ventricular pacing pulses, and electrodes 154 and 155 may allow for delivery of one or more ventricular cardioversion/defibrillation pulses. In an example, the lead 108B may include only three electrodes 152, 154 and 155. The electrodes 152 and 154 may be used for sensing or delivery of one or more ventricular pacing pulses, and the electrodes 154 and 155 may be used for delivery of one or more ventricular cardioversion or defibrillation pulses. The lead 108C may include a proximal end that may be connected to the IMB 110 and a distal end that may be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C may include an electrode 161 that may be located at a distal end of the lead 108C and another electrode 162 that may be located near the electrode 161. The electrodes 161 and 162 may be electrically connected to the IMD 110 such as via separate conductors in the lead 108C such as to allow for sensing of the LV electrogram and allow delivery of one or more resynchronization pacing pulses from the LV. Additional electrodes may be included in or along the lead 108C. In an example, as illustrated in FIG. 1, a third electrode 163 and a fourth electrode 164 may be included in the lead 108. In some examples (not shown in FIG. 1), at least one of the leads 108A-C, or an additional lead other than the leads 108A-C, may be implanted under the skin surface without being within at least one heart chamber, or at or close to heart tissue.

The IMB 110 may include an electronic circuit that may sense a physiological signal. The physiological signal may include an electrogram or a signal representing mechanical function of the heart 105. The hermetically sealed can housing 112 may function as an electrode such as for sensing or pulse delivery. For example, an electrode from one or more of the leads 108A-C may be used together with the can housing 112 such as for unipolar sensing of an electrogram or for delivering one or more pacing pulses. A defibrillation electrode from the lead 108B may be used together with the can housing 112 such as for delivering one or more cardioversion/defibrillation pulses. In an example, the IMD 110 may sense impedance such as between electrodes located on one or more of the leads 108A-C or the can housing 112. The IMD 110 may be configured to inject current between a pair of electrodes, sense the resultant voltage between the same or different pair of electrodes, and determine impedance using Ohm's Law. The impedance may be sensed in a bipolar configuration in which the same pair of electrodes may be used for injecting current and sensing voltage, a tripolar configuration in which the pair of electrodes for current injection and the pair of electrodes for voltage sensing may share a common electrode, or tetrapolar configuration in which the electrodes used for current injection may be distinct from the electrodes used for voltage sensing. In an example, the IMB 110 may be configured to inject current between an electrode on the RV lead 108B and the can housing 112, and to sense the resultant voltage between the same electrodes or between a different electrode on the RV lead 108B and the can housing 112. A physiological signal may be sensed from one or more physiological sensors that may be integrated within the IMB 110. The IMD 110 may also be configured to sense a physiological signal from one or more external physiological sensors or one or more external electrodes that may be coupled to the IMB 110. Examples of the physiological signal may include one or more of thoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature.

The arrangement and functions of these leads and electrodes are described above by way of non-limiting example and not by way of limitation. Depending on the need of the patient and the capability of the implantable device, other arrangements and uses of these leads and electrodes are contemplated.

As illustrated, the CRM system 100 may include a cardiac arrhythmia detector 113 for detecting an arrhythmic event such as an atrial fibrillation (AF) episode using a physiological signal detected from the patient. The cardiac arrhythmia detector 113 may determine a heart rate (HR) pattern or a cardiac cycle length (CL) pattern using heart rates or cycle lengths determined from the physiological signal. Using various HR or CL patterns, the cardiac arrhythmia detector 113 may generate a repetitiveness indicator indicative of randomness of the heart rates or cycle lengths. A more repetitive CL or HR pattern may weigh against AF, while a less repetitive or more random CL or HR pattern may weigh toward AF. The cardiac arrhythmia detector 113 may detect AF based on the repetitiveness indicator. In some examples, the cardiac arrhythmia detector 113 may further discriminate AF from other types of arrhythmias such as arrhythmias with atrio-ventricular conduction abnormalities. Examples of the cardiac arrhythmia detector 113 are described below, such as with reference to FIGS. 2-5.

The external system 120 may allow for programming of the IMB 110 and may receive information about one or more signals acquired by IMB 110, such as may be received via a communication link 103. The external system 120 may include a local external IMB programmer. The external system 120 may include a remote patient management system that may monitor patient status or adjust one or more therapies such as from a remote location.

The communication link 103 may include one or more of an inductive telemetry link, a radio-frequency telemetry link, or a telecommunication link, such as an internet connection. The communication link 103 may provide for data transmission between the IMB 110 and the external system 120. The transmitted data may include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that may include physiological data acquisition such as using programmably specifiable sensing electrodes and configuration, device self-diagnostic test, or delivery of one or more therapies.

The cardiac arrhythmia detector 113, although as illustrated in FIG. 1 included within the IMD 110, may alternatively be implemented in a subcutaneously implanted device, a wearable external device, a neural stimulator, a drug delivery device, a biological therapy device, or one or more diagnostic devices. In some examples, the cardiac arrhythmia detector 113 may be implemented in the external system 120. The external system 120 may include a health status monitor, which may be configured to detect worsening heart failure (WHF) using data extracted from the IMB 110 or data stored in a memory within the external system 120. The external system 120 may include a user interface that may display information about detection of AF or other cardiac events. In an example, portions of the cardiac arrhythmia detector 113 may be distributed between the IMD 110 and the external system 120.

Portions of the IMB 110 or the external system 120 may be implemented using hardware, software, or any combination of hardware and software. Portions of the IMB 110 or the external system 120 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals. While described with reference to the IMB 110, the CRM system 100 may include a subcutaneous medical device (e.g., subcutaneous ICD, subcutaneous diagnostic device), wearable medical devices (e.g., patch based sensing device), or other external medical devices.

Figure 2:
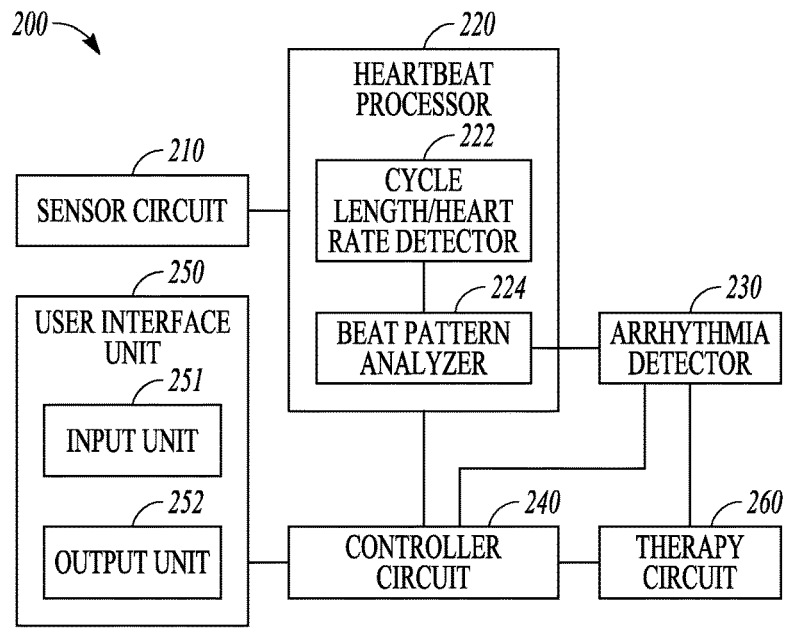
FIG. 2 illustrates generally an example of an arrhythmia detection system configured to detect a cardiac arrhythmia such as atrial fibrillation (AF) from a patient.

FIG. 2 illustrates generally an example of an arrhythmia detection system 200 that may be configured to detect a cardiac arrhythmia from a patient, such as an atrial fibrillation (AF) episode. The arrhythmia detection system 200 may be an embodiment of the cardiac arrhythmia detector 113. The arrhythmia detection system 200 may include one or more of a sensor circuit 210, a heartbeat processor 220, an arrhythmia detector 230, a controller circuit 240, and a user interface unit 250. The arrhythmia detection system 200 may be configured as a cardiac monitor or diagnostic device for monitoring patient health status. In some examples, the arrhythmia detection system 200 may additionally include an optional therapy circuit 260 and configured as a therapeutic device.

The sensor circuit 210 may include a sense amplifier circuit to sense a physiological signal sensed from a patient via one or more implantable, wearable, or otherwise ambulatory sensors or electrodes associated with the patient. Examples of the physiological signals may include surface electrocardiography (ECG) such as sensed from electrodes on the body surface, subcutaneous ECG such as sensed from electrodes placed under the skin, intracardiac electrogram (EGM) sensed from the one or more electrodes of the leads 108A-C or the can housing 112, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit 210 may include one or more other sub-circuits to digitize, filter, or perform other signal conditioning operations on the received physiological signal.

In some examples, the physiological signals may be stored in a storage device such as an electronic medical record (EMR) system. The sensor circuit 210 may be configured to retrieve a physiological signal from the storage device in response to a command signal that is provided by a system user, or automatically generated in response to occurrence of a specified event.

The heartbeat processor 220 may be coupled to the sensor circuit 210 to analyze beat patterns. The heartbeat processor 220 may include a cycle length/heart rate detector 222 and a beat pattern analyzer 224. In an example, the sensor circuit 210 may sense a cardiac electrical signal such as a ECG, a subcutaneous ECG, or an intracardiac EGM, and the cycle length/heart rate detector 222 may detect from the cardiac electrical signal electrophysiological events indicative of cardiac depolarization or repolarization at a portion of the heart, such as an atrium, a ventricle, a His-bundle, or a septum. Examples of the sensed electrophysiological events may include P wave, Q wave, R wave, QRS complex, or T wave in a surface or subcutaneous ECG or an intracardiac EGM. The sensor circuit 210 may additionally or alternatively include one or more sensors configured to sense cardiac mechanical activity indicative of heart contractions, and the cycle length/heart rate detector 222 may detect from the sensed cardiac mechanical activity mechano-physiological events indicative of one or more of atrial contraction, ventricular contraction, end of filling, end of emptying, or other specified phase during a cardiac contraction cycle. Examples of the sensors for sensing cardiac mechanical activity may include an accelerometer or a microphone configured to sense a heart sound signal or an endocardial acceleration signal from the heart, an impedance sensor configured to sense cyclic changes in cardiac impedance as a result of cardiac contractions, or a blood pressure sensor or a blood flow sensor for sensing pulsatile arterial pressure or flow as a result of cyclic cardiac contractions and opening/closure of heart valves, among other sensors. Examples of the mechano-physiological events may include: S1, S2, S3, or S4 heart sound from the sensed heart sound signal, peak or trough impedance from the cardiac impedance signal, or peak or trough blood pressure from the blood pressure signal, among others.

The cycle length/heart rate detector 222 may detect HR or CL using the detected electrophysiological or mechano-physiological events. In an example, the CL, in a unit of second or millisecond, may be measured a time interval between two adjacent R waves (R-R interval) or P waves (P-P interval), or between adjacent impedance peaks or adjacent impedance troughs from the cardiac impedance signal, or an interval between two adjacent blood pressure peaks (i.e., systolic pressure) or adjacent blood pressure troughs (i.e., diastolic pressure) from the blood pressure signal, among others. The HR, in a unit of beats per minute (bpm), may be computed using the CL such as according to HR=60 seconds/CL.

The beat pattern analyzer 224, which may be coupled to the cycle length/heart rate detector 220, may recognize a plurality of beat patterns using the HR or CL measurements. The beat patterns indicate temporal relationships between the two or more consecutive cardiac cycles. In an example, the beat patterns may be recognized using respective two or more consecutive CLs, including a consecutively ascending CL pattern characterized by lengthening of CL of the present cardiac cycle from the immediately previous cardiac cycle, a consecutively descending CL pattern characterized by shortening of CL of the present cardiac cycle from the immediately previous cardiac cycle, or an identical CL pattern characterized by consecutive cardiac cycles having substantially identical cycle length, among other beat patterns. The beat pattern analyzer 224 may perform a statistical analysis of a plurality of beat patterns, and generate a repetitiveness indicator of the beat pattern indicating a degree of randomness of the determined CLs. Examples of the beat pattern analyzer 224 are discussed below, such as with reference to FIGS. 3A-B and 4.

The arrhythmia detector 230 may be coupled to the beat pattern analyzer 224 to detect a cardiac arrhythmia at least based on the repetitiveness indicator of the beat patterns. Examples of cardiac arrhythmias may include atrial fibrillation (AF), atrial flutter (AFL), atrial tachycardia, paroxysmal supraventricular tachycardia (PSVT), Wolff-Parkinson-White (WPW) syndrome, ventricular tachycardia, ventricular fibrillation, bradycardia, or sinus pauses, among others. In an example, the arrhythmia detector 230 may be configured to discriminate between AF and unstable but substantially organized rhythms such as cardia rhythms with various degrees of atrio-ventricular conduction abnormalities (such as Wenckebach rhythm) or premature atrial contractions (PACs). Although such unstable and organized rhythms may manifest variable HR or CL which may resemble atrial arrhythmias such as AF, they nevertheless may have more organized (or less random) beat patterns and thus a higher degree of repetitiveness than a typical AF episode. In an example, the arrhythmia detector 230 may trend the repetitiveness indicator over time. If the repetitiveness indicator falls below a specified threshold, a more disorganized beat pattern is indicated and an AF episode is detected. In another example, the arrhythmia detector 230 may include a first arrhythmia detector and a different second arrhythmia detector. The first arrhythmia detector may be sensitive but less specific to AF, and detects AF based on HR or CL stability. The second arrhythmia detector may be more specific to AF, and employs a beat pattern and repetitiveness based method to confirm, reject, or other modify the detection provided by the first arrhythmia detector. The second arrhythmia detector may additionally distinguish an AF episode from an unstable and organized rhythm. Examples of the arrhythmia detector 230 are discussed below, such as with reference to FIG. 5.

As illustrated in FIG. 2, the heartbeat processor 220 or the arrhythmia detector 230 may respectively include circuit sets comprising one or more other circuits or sub-circuits. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

In various examples, the heartbeat processor 220 or the arrhythmia detector 230 may be implemented as a part of a microprocessor circuit. The microprocessor circuit may be a dedicated processor such as a digital signal processor, application specific integrated circuit (ASIC), microprocessor, or other type of processor for processing information including the physiological signals received from the sensor circuit 210. Alternatively, the microprocessor circuit may be a general purpose processor that may receive and execute a set of instructions of performing the functions, methods, or techniques described herein.

The controller circuit 240 may control the operations of the sensor circuit 210, the heartbeat processor 220, the arrhythmia detector 230, the user interface unit 250, and the data and instruction flow between these components. The controller circuit 240 may control the heartbeat pattern analysis and arrhythmia detection, and configure the user interface unit 250 to output the beat patterns, the repetitiveness indicator, or the detected cardiac arrhythmia to a user or a process. The user interface unit 250 may include an input unit 251 and an output unit 252. In an example, at least a portion of the user interface unit 250 may be implemented in the external system 120. The input unit 251 may receive a user's programming input, such as respective parameters for beat pattern analysis or parameters for arrhythmia detection. The input unit 251 may include an input device such as a keyboard, on-screen keyboard, mouse, trackball, touchpad, touch-screen, or other pointing or navigating devices. The input device may enable a system user to program the parameters used for sensing the physiological signals, detecting the arrhythmias, and generating alerts, among others. The output unit 252 may generate a human-perceptible presentation of information including one or more of the detection of the target cardiac arrhythmia, confidence indicators associated with the detected arrhythmic events, alerts generated for the detected arrhythmias, or other system information. The output unit 252 may include a display for displaying the information. The information may be presented in a table, a chart, a diagram, or any other types of textual, tabular, or graphical presentation formats, for displaying to a system user. The presentation of the output information may include audio or other media format to alert the system user of the detected physiological events.

The optional therapy circuit 260 may be configured to deliver a therapy to the patient in response to the detection of the arrhythmia. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 260 may modify an existing therapy, such as adjust a stimulation parameter or drug dosage.

Figure 3A:
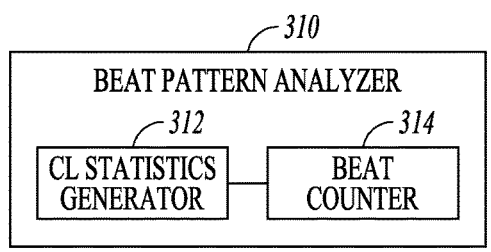
FIGS. 3A-B illustrate generally examples of beat pattern analyzer for analyzing the beat patterns to determine a degree of randomness of a cardiac rhythm.
Figure 3B:
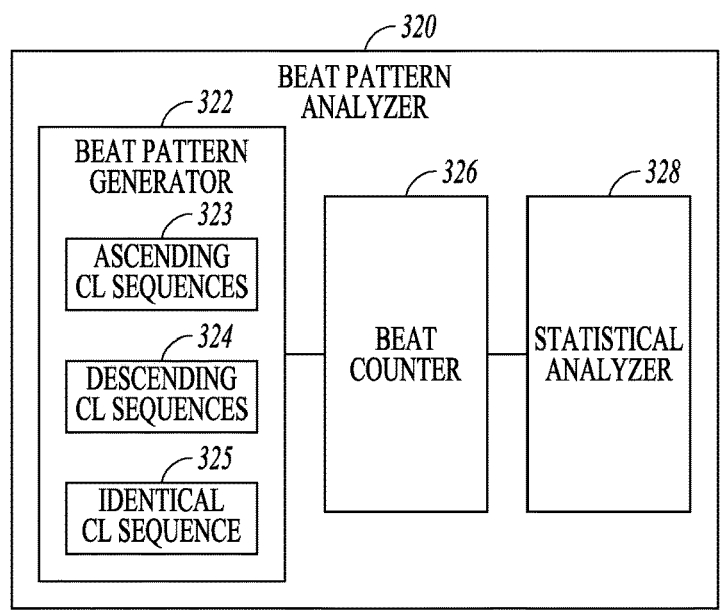

FIGS. 3A-B illustrate generally examples of beat pattern analyzer for analyzing the beat patterns to determine a degree of randomness of a cardiac rhythm. Beat pattern analyzer 310 as illustrated in FIG. 3A and beat pattern analyzer 320 as illustrated in FIG. 3B may each be an embodiment of the beat pattern analyzer 224.

The beat pattern analyzer 310 may include a cycle length statistics generator 312 and a beat counter 314. The cycle length statistics generator 312 may generate a beat pattern including a cycle length statistic based on cycle lengths of a plurality of consecutive cardiac cycles. Examples of the CL statistic may include one of a maximum cycle length (maxCL), a minimum cycle length (minCL), a median cycle length (medCL), or an average cycle length (avgCL), each computed from a plurality of consecutive CLs within respective time windows. The beat counter 314, coupled to the CL statistics generator, may generate a repetitiveness indicator including a percentage of the computed CL statistics that are substantially identical within a specified tolerance.

In an example, in analyzing a cardiac rhythm from a physiological signal, the CL statistics generator 312 may apply multiple data windows $\{W\}=(W1, W2, \ldots, Wn)$ to the consecutive HRs or CLs, and compute the statistics such as maxCL, minCL, medCL, or avgCL using the HRs or CLs within the data windows $\{W\}$. The data window may be defined as a specified time duration or a specified number of cardiac cycles. The beat counter 314 may identify and count the data windows associated with the CL statistics satisfying a specified condition such as being substantially identical within a specified tolerance. In an example where the maxCL statistics $\{maxCL\}=(maxCL1, maxCL2, \ldots, maxCLn)$ are computed respectively for the data windows $\{W\}=(W1, W2, \ldots, Wn)$, the substantially identical CL statistics may include those falling within a specified range defined a lower bound (LB) and an upper bound (UB) of maxCL. The LB and UB may respectively be determined using a central tendency $\mu$ (e.g., an average) and a standard deviation $\sigma$ of all or a portion of $\{maxCL\}$. In an example, $LB=\mu-c1*\sigma$ and $UB=\mu+c2*\sigma$, where c1 and c2 are constants controlling the tolerance for identicalness. In an example, the c1 and c2 may be approximately 10-20%. The beat counter 314 may determine a relative count, such as a fraction or a percentage, of the maxCL that falls within the range defined by the LB and UB. The arrhythmia detector 230 may detect the AF when the percentage of the CL statistics fall below an AF threshold. In an example, the AF threshold is approximately 50%. Examples of the repetitiveness indicator based on CL statistics are discussed below, such as with reference to FIG. 4.

The beat pattern analyzer 320 as illustrated in FIG. 3B may include a beat pattern generator 322, a beat counter 326, and a statistical analyzer 328. The beat pattern generator 322 may generate one or more beat patterns indicative of temporal relationship between two or more consecutive cardiac cycles. By way of non-limiting example, the beat patterns may include one or more ascending CL sequences 323 of consecutive cardiac cycles progressively increasing by at least a specified step size $\delta_1$ and descending CL sequences 324 of two or more consecutive cardiac cycles progressively decreasing by at least a specified step size $\delta_2$. The step size $\delta_2$ may be different than the step size $\delta_1$.

The beat pattern generator 322 may compute various beat patterns in an automated process, which includes computing a difference CL sequence $\{\Delta CL\}=\{\Delta CL1, \Delta CL2, \ldots, \Delta ELn\}$ where $\Delta CLi$ denotes a difference between two adjacent cycle lengths $CL(i+1)$ and $CL(i)$, that is, $\Delta CLi=CL(i+1)-CL(i)$. The difference $\Delta CLi$ may be assigned a symbol "L" denoting CL lengthening if $\Delta CLi$ is positive and $\Delta CLi>\delta_1$, or a symbol "S" denoting CL shortening if $\Delta CLi$ is negative and $\Delta CLi<\delta_2$, or a symbol "I" denoting identical CL if $\delta_2<\Delta CLi<\delta_1$. As such, the difference CL sequence $\{\Delta CL\}$ may then be transformed into a symbolic sequence comprising one or more of "S", "L", and "I".

In an example, the ascending CL sequences 323 may include an ascending sequence of two consecutive cardiac cycles with cycle lengths CL1<CL2, represented by an "L" sequence or a "+1" pattern indicating CL2 longer than the previous CL1 by at least $\delta_1$. In another example, the ascending CL sequences 323 may include an ascending sequence of three consecutive cardiac cycles with cycle lengths CL1<CL2<CL3, represented by an "LL" sequence or a "+2" pattern indicating CL2 longer than the previous CL1 by at least $\delta_1$, and CL3 longer than the previous CL2 by at least $\delta_1$. In an example, the descending CL sequences 324 may include a descending sequence of two consecutive cardiac cycles with cycle lengths CL1>CL2, represented by an "S" sequence or a "-1" pattern indicating CL2 shorter than the previous CL1 by at least $\delta_2$. In another example, the descending CL sequences 324 may include a descending sequence of three consecutive cardiac cycles with cycle lengths CL1>CL2>CL3, represented by an "SS" sequence or a "-2" pattern indicating CL2 shorter than the previous CL1 by at least $\delta_2$, and CL3 shorter than the previous CL2 by at least $\delta_2$. In some examples, the beat patterns generated by the beat pattern generator 322 may additionally include an identical CL sequence 325 represented by an "I" sequence or a "0" pattern. The identical CL sequence 325 may include two or more consecutive cardiac cycles of substantially identical cycle length within a specified tolerance, such as the difference between the consecutive cycle lengths CL1 and CL2 falling between $\delta_1$ and $\delta_2$, that is, $\delta_2<CL2-CL1<\delta_1$. Table 1 below shows examples of the symbolic sequence and the corresponding beat patterns.

TABLE 1

| Sequence | Beat Pattern |
|---|---|
| SSS | -3 |
| SS | -2 |
| S | -1 |
| I | 0 |

TABLE 1-continued

| Sequence | Beat Pattern |
|---|---|
| L | +1 |
| LL | +2 |
| LLL | +3 |

The beat counter 326 may identify and count various beat patterns from a sequence of HRs or CLs measured from a physiological signal. For example, a symbolic sequence of X=LSSLSSLLSSI that is transformed from $\{\Delta CL\}$ includes three "SS" sequences, one "I" sequence, two "L" sequences, and one "LL" sequence. Accordingly, the beat counter 326 may determine pattern counts as shown in Table 2.

TABLE 2

| Sequence | Beat Pattern | Pattern counts |
|---|---|---|
| SSS | -3 | 0 |
| SS | -2 | 3 |
| S | -1 | 0 |
| I | 0 | 1 |
| L | +1 | 2 |
| LL | +2 | 1 |
| LLL | +3 | 0 |

The statistical analyzer 328 may determine a repetitiveness indicator based on the beat pattern counts such as those illustrated in Table 2. In an example, positive beat patterns, such as corresponding to beat patterns of "+1", "+2", "+3" etc. are accumulated to produce a first count (N1) of ascending CL sequences. Similarly, negative beat patterns, such as corresponding to beat patterns of "-1", "-2", "-3" etc. are accumulated to produce a second count (N2) of descending CL sequences. For the symbolic sequence X discussed above, according to Table 2, the first and second counts may be determined as N1=2+1=3, and N2=3. In some examples, the "I" sequences or "0" beat patterns, if any, may be counted towards either the ascending or the descending CL sequences, such that the first or second count (N1 or N2) may include a count of the "I" sequences or "0" beat patterns.

The statistical analyzer 328 may use N1 and N2 to determine one or more composite measures, including an accumulative observed count (R), an expected count (E), and a standard deviation (SD) of counts of the ascending and descending CL sequences each using N1 and N2. These composite measures may be determined according to Equation (1) below:

$$\begin{cases} R = N1 + N2 \\ E = \dfrac{2N1N2}{R} + 1 \\ SD = \dfrac{1}{R}\sqrt{\dfrac{2N1N2(2N1N2 - R)}{R-1}} \end{cases} \quad (1)$$

The statistical analyzer 328 may determine a repetitiveness indicator using the composite measures O, E and SD, such as a Z statistic according to Equation (2) below:

$$Z=(R-E)/SD \quad (2)$$

The Z statistic as computed according to Equation (2) may indicate a degree of randomness of the CL or HR sequence being analyzed. A larger Z statistic weighs toward more organized (i.e., less random) CL or HR sequence, thus indicating the underlying rhythm being less likely an AF rhythm. Conversely, a smaller Z statistic weighs toward more random or disorganized CL or HR sequence, thus indicating the underlying rhythm being more likely an AF rhythm. The arrhythmia detector 230 may compare the repetitiveness indicator Z to an AF threshold, and detect an AF episode when the Z statistic falls below an AF threshold. In some examples, if R is substantially larger than E (e.g., R is greater than E by at least approximately 20), then the arrhythmia detector 230 may decide that the underlying rhythm is an organized rhythm, rather than an AF episode.

When N1 and N2 are sufficiently large (such as when N1 and N2 are each greater than 10), the repetitiveness indicator Z may follow a standard normal distribution, with a mean of zero and standard deviation of one. The repetitiveness indicator Z may be compared to a threshold representing a specified significance level (such as X %) that the underlying rhythm is not from a random process. For example, according to the standard normal distribution, at 5% significance level, the threshold is 1.96. If the absolute value of the Z statistic is greater than 1.96, then with a 95% confidence, the underlying rhythm is decided not from a random process. That is, the cardia rhythm under analysis is not an AF episode.

Figure 4:
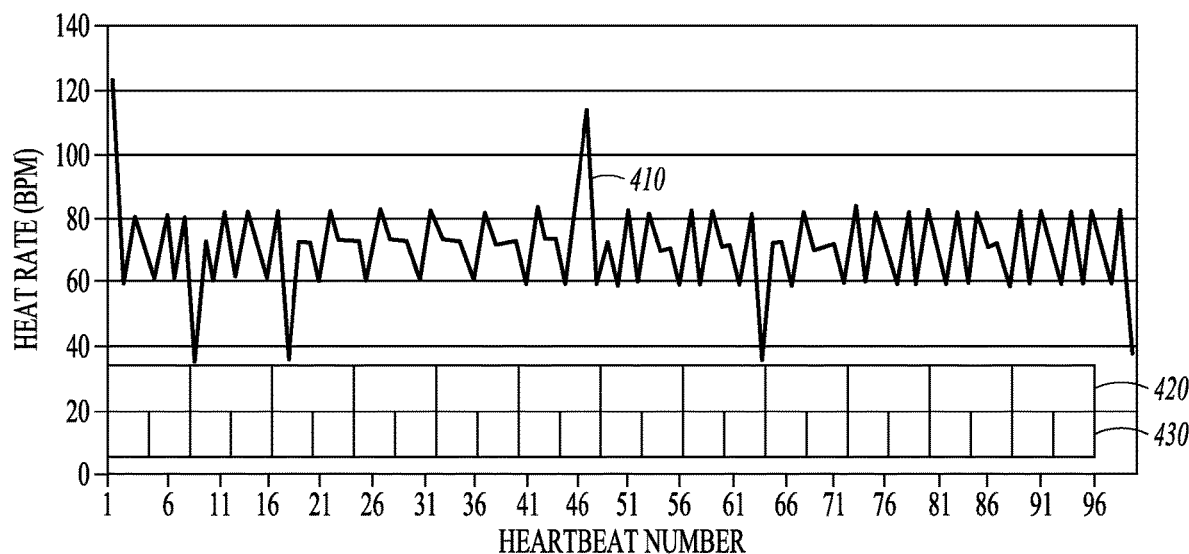
FIG. 4 illustrates generally an example of repetitiveness indicator based on cardiac cycle length statistics.

FIG. 4 illustrates generally an example of repetitiveness indicator based on CL statistics such as determined by the CL statistics generator 312 as shown in FIG. 3A. A heart rate (HR) sequence 410 may be generated by the cycle length/heart rate detector 222 such as from a physiological signal sensed from a patient or retrieved from a storage device. The HR sequence 410 comprises heart rates (in bpm, on the y-axis) determined from cycle lengths of consecutive cardiac cycles (on the x-axis) detected from the physiological signal. By way of non-limiting examples, FIG. 4 shows approximately 100 cardiac cycles or heartbeats for use in determining if the underlying rhythm is an AF episode or otherwise a more organized cardiac rhythm.

The cycle length statistics generator 312 may apply a first set of data windows 420 to the HR sequence 410, and compute a maximum cycle length (maxCL) within each data of the data windows 420, resulting in maxCL statistics {maxCL}=(maxCL1, maxCL2, . . . , maxCLn). Alternatively or additionally, the cycle length statistics generator 312 may apply a second set of data windows 430 to the HR sequence 410, and compute a minimum cycle length (minCL) within each of the data windows 430, resulting in minCL statistics {minCL}=(minCL1, minCL2, . . . , minCLm). The length of the data windows 420 or 430 may be defined as a specified time duration (such as approximately 1-5 seconds) or a specified number of cardiac cycles (such as approximately 3-10 consecutive cardiac cycles). The first data windows 420 may have different durations than the second data windows 430. By way of non-limiting example, and as illustrated in FIG. 4, the first data windows 420 each has a duration of six consecutive cardiac cycles, and the second data windows 430 each has a duration of three consecutive cardiac cycles. In some examples, at least some of the data windows 420 may be overlapped by a specified amount, or at least some of the data windows 430 may be overlapped by a specified amount.

The beat counter 314 may identify and count, out of the first set of data windows 420, the data windows having substantially identical maxCL, such as within a specified lower and upper bounds as previously discussed with reference to FIG. 3A. The beat counter 314 may additionally or alternatively identify and count, out of the second set of data windows 430, the data windows having substantially identical minCL, such as within a specified lower and upper bounds as discussed with reference to FIG. 3A. The arrhythmia detector 230 may detect an AF episode by comparing a percentage of the computed cycle length statistics to an AF threshold, such as approximately 50%. In an example, the beat counter 314 may determine 80% of the first data windows 420 have substantially identical maxCL values, and/or 70% of the second data windows 430 have substantially identical minCL values. Because more than 50% of the first data windows 420 have substantially identical maxCL, or more than 50% of the second data windows 430 have substantially identical minCL, the arrhythmia detector 230 decides that the heart rate sequence 410 is organized, and the underlying rhythm is not an AF episode. In an example, the arrhythmia detector 230 may generate a composite statistic using two or more of maxCL, minCL, medCL, or avgCL, among other cycle length statistics. The composite statistic may be determined using a linear or nonlinear combination including a voting, weighted combination, decision trees, or neural networks, among others.

Figure 5:
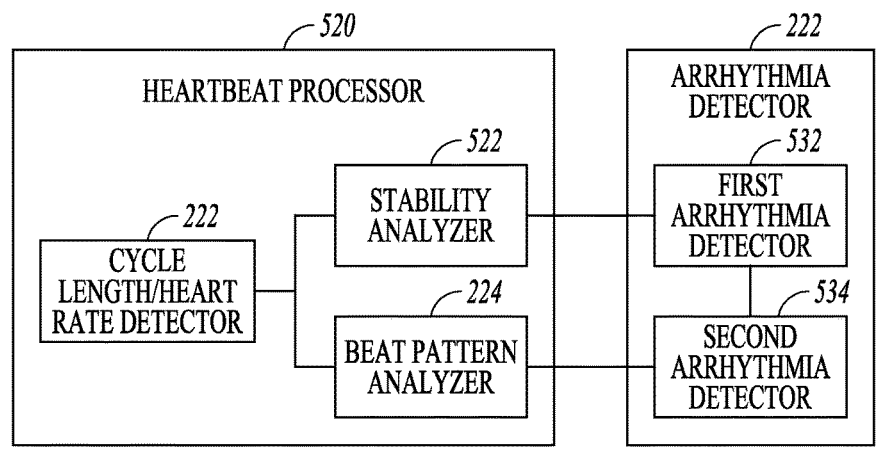
FIG. 5 illustrates generally an example of portions of an arrhythmia detector system such as for detecting an AF episode.

FIG. 5 illustrates generally an example of portions of an arrhythmia detector system such as for detecting an AF episode. The system portion may include a heartbeat processor 520 and an arrhythmia detector 530, which are respectively embodiments of the heartbeat processor 220 and an arrhythmia detector 230. The heartbeat processor 520 may include the cycle length/heart rate detector 222 and the beat pattern analyzer 224, which are described previously with reference to FIG. 2. As illustrated in FIG. 5, the heartbeat processor 520 may additionally include a stability analyzer 522 configured to calculate a stability of the cycle lengths or heart rates. In an example, the stability may include difference, variance, standard deviation, or other higher-order statistics that characterize the variability of the cycle lengths or heart rates. In another example, the stability may be derived from Lorenz plot (LP) of the HRs or CLs. The LP is a scatterplot of the present CL or HR as a function of the preceding one or more CLs or HRs. The LP-based stability may include geometric indices generated from the LP of the CLs or HRs, such as maximal length of the LP shape, maximal width of the LP shape, a density or spreadness measure of the LP scatterplots, among others.

The arrhythmia detector 530 may include a first arrhythmia detector 532 and a second arrhythmia detector 534. The first arrhythmia detector 532 may be coupled to the stability analyzer 522 to perform an initial detection of AF using the stability of the CLs or HRs. In an example, the stability analyzer 522 may classify the HRs or CLs into one of a plurality of beat classes including a stable beat class, an unstable beat class, and a random beat class. The stability may be computed as a relative quantity, such as a difference, a ratio, a proportion, or a percentage, using the beat counts of the stable beats, the unstable beats, or the random beats. Examples of the relative quantity may include a ratio of the number of unstable beats to a sum of the numbers of the stable and unstable beats, or a ratio of the number of random beats to a sum of the numbers of the stable and unstable beats. The first arrhythmia detector 532 may detect the AF episode in response to the relative quantity satisfying a specified condition, such as those disclosed in the commonly assigned Mahajan et al. U.S. Patent Application 20160220139, entitled "PHYSIOLOGIC EVENT DETECTION AND DATA STORAGE," filed on Jan. 27, 2016, which is hereby incorporated by reference in its entirety, including its disclosure of beats classes and AF detection using at least the beat classes.

In an example, the stability analyzer 522 may determine the stability based on a HR or CL distribution such as a HR histogram or a CL histogram. The HR histogram or CL histogram may include percentages of the heart beats during a specified time period that fall within each of a plurality of heart rate bins. Each heart rate bin defines a range of HRs or CLs. The indicator may include a mode of the HR or CL, such as a histogram bin (or a representative heart rate value of that histogram bin) that includes the most heart beats with corresponding HRs or CLs falling within that histogram bin. The indicator may alternatively or additionally include a heart rate density index (HRDI), which may be calculated as a percentage of the heart beats falling within the histogram bin including the mode of the heart rates. The first arrhythmia detector 532 may detect the target cardiac arrhythmia such as an AF episode in response to the mode of the heart rate or the HRDI each satisfies a specified condition, such as those disclosed in the commonly assigned Mahajan et al. U.S. patent application Ser. No. 15/082,440, entitled "ATRIAL FIBRILLATION DETECTION," filed May 28, 2016, which is hereby incorporated by reference in its entirety, including its disclosure of the HRDI and the AF detection using at least the HRDI.

The first arrhythmia detector may additionally or alternatively detect AF using morphology of a plurality of heart beats from the physiological signal. The morphology may include a plurality of morphological features such as samples selected from a portion of a waveform of the signal metric within a beat (or a cardiac cycle). In an example, the morphological features may include characteristic points of the waveform such as a peak, a trough, an inflection point, or one or more intermediate points between the characteristic points. The first arrhythmia detector 532 may receive from a user such as via the user interface unit 250, or retrieve from a memory device, a template that represents the morphology of the same signal metric that is obtained during a known rhythm such as a sinus rhythm or a specified arrhythmia such as AF. The first arrhythmia detector 532 may compare the morphology measurements of the plurality of beats to the template, and compute a similarity score between the morphology measurements and template. Examples of the similarity score may include a correlation, a sum of differences between the morphology measurements and scaled template, or a distance measure in a multi-dimensional signal feature space. In an example, the arrhythmia detector 532 may dynamically update the template using the morphology measurements of previous one or more beats that are morphologically similar to the received or retrieved template (such as the similarity score falling within a specified range). The first arrhythmia detector 532 may detect the cardiac arrhythmia in response to the similarity score satisfying a specified condition, such as when the difference falls below a specified detection threshold.

The second arrhythmia detector 534, which is an embodiment of the arrhythmia detector 230, may be coupled to the first arrhythmia detector 532 and the beat pattern analyzer 224 and detect AF using at least the repetitiveness indicator of the beat pattern, such as the CL statistics-based repetitiveness indicator (as shown in FIG. 3A) or the ascending or descending CL sequences-based repetitiveness indicator (as shown in FIG. 3B). In an example, the first arrhythmia detector 532 may be sensitive but less specific to AF, and the second arrhythmia detector 534 may be more specific to AF. The second arrhythmia detector 534 may use the repetitiveness indicator to affirm, reject, or modify the AF detection as provided by the first arrhythmia detector 532, such as to reduce false positive detections of AF episodes. In an example, the second arrhythmia detector 534 may be configured to discriminate between an AF episode and an unstable but substantially organized rhythms such as cardia rhythms with various degrees of atrio-ventricular conduction abnormalities (e.g., Wenckebach rhythms), or premature atrial contractions (PACs).

In various examples, the second arrhythmia detector 534 may perform AF detection when a low confidence is associated with the detection from the first arrhythmia detector 532. The first and second arrhythmia detectors 532 and 534 may have different computational power. In an example, the second arrhythmia detector 534 may detect cardiac arrhythmia using a computationally more intensive algorithm, or to process larger amount of data for detecting the arrhythmic event than the first arrhythmia detector 532. In an example, the second arrhythmia detector 534 may perform retrospective analysis of historical physiological data collected from the patient, while the first arrhythmia detector 532 may perform real-time AF detection.

Although the second arrhythmia detector 534 is shown to be within the arrhythmia detector 530, this is meant only by example and not limitation. The second arrhythmia detector 534 may alternatively be implemented in a separate device than the first arrhythmia detector 232, such as in a programmer, a hand-held, wearable, or other portable device, or a server. In an example, portions of the sub-circuits in the arrhythmia detector 530, such as the first arrhythmia detector 532 and the second arrhythmia detector 534, may be distributed between the IMD 110 and the external system 120.

Figure 6:
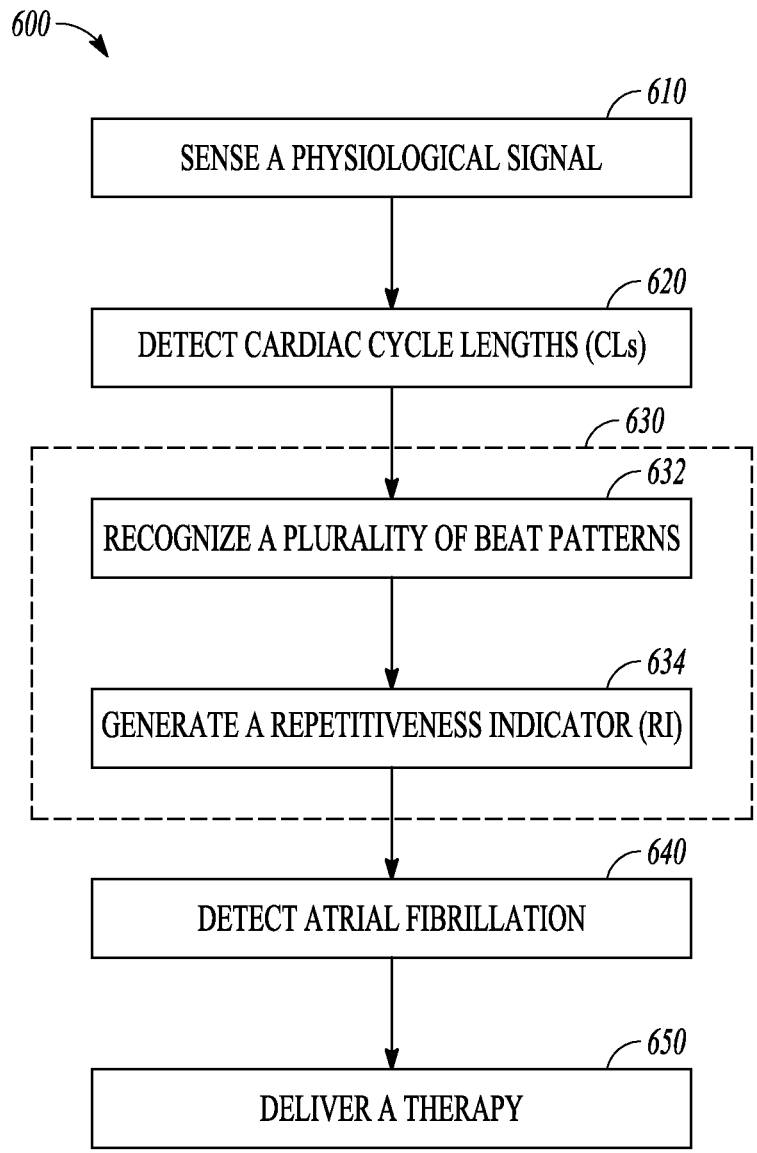
FIG. 6 illustrates generally an example of a method for detecting a target cardiac arrhythmia from a patient.

FIG. 6 illustrates generally an example of a method 600 for detecting a cardiac arrhythmia from a patient. Examples of cardiac arrhythmias may include atrial fibrillation (AF), atrial flutter (AFL), atrial tachycardia, paroxysmal supraventricular tachycardia (PSVT), Wolff-Parkinson-White (WPW) syndrome, ventricular tachycardia, ventricular fibrillation, bradycardia, or sinus pauses, among others. The method 600 may be implemented and executed in an ambulatory medical device such as an implantable or wearable medical device, or in a remote patient management system. In an example, the method 600 may be performed by the cardiac arrhythmia detector 113 or any embodiment thereof, or by the external system 120.

The method 600 begins at 610 by sensing a physiological signal from a patient. The physiological signals may include cardiac electrical signals such as electrocardiography (ECG) or intracardiac electrogram (EGM). The physiological signals may additionally or alternatively include signals indicative of cardiac mechanical activity, including thoracic or cardiac impedance signal, arterial pressure signal, pulmonary artery pressure signal, left atrial pressure signal, RV pressure signal, LV coronary pressure signal, heart sounds or endocardial acceleration signal, physiological response to activity, apnea hypopnea index, one or more respiration signals such as a respiration rate signal or a tidal volume signal, among others. The sensed physiological signal may be pre-processed, including one or more of signal amplification, digitization, filtering, or other signal conditioning operations. In an example, a plurality of electrophysiological or mechano-physiological events indicative of heart beats may be detected from the pre-processed physiological signal. In some examples, signal metrics such as timing parameters, or statistical or morphological parameters associated with the beats may be detected from the sensed physiological signal.

At 620, a cardiac cycle length (CL) or heart rate (HR) may be detected using the electrophysiological or mechano-physiological events. The CL may be measured as an interval between two adjacent R waves (R-R interval) or P waves (P-P interval), an interval between adjacent impedance peaks or adjacent impedance troughs from the cardiac impedance signal, or an interval between two adjacent blood pressure peaks (i.e., systolic pressure) or adjacent blood pressure troughs (i.e., diastolic pressure) from the blood pressure signal, among others. The HR, in a unit of beats per minute (bpm), may be computed according to HR=60 seconds/CL where CL is measured in a unit of seconds.

At 630, the HR or CL may be analyzed such as by using one of the beat pattern analyzers 224, 310, or 320 as illustrated in FIGS. 2 and 3A-B. The analysis may include computing a plurality of beat patterns at 632 based on the HR or CL measurements, and generating a repetitiveness indicator using the beat patterns at 634. The beat patterns may indicate a temporal relationship between the two or more consecutive cardiac cycles. In an example, at 632 the beat patterns may include a cycle length statistic, such as one of a maximum cycle length (maxCL), a minimum cycle length (minCL), a median cycle length (medCL), or an average cycle length (avgCL), each computed using CL of a plurality of consecutive cardiac cycles within a time window. In a non-limiting example as illustrated in FIG. 4, the data windows used for computing one cycle length statistic (e.g., maxCL) may have different length than the data windows for computing another cycle length statistic (e.g., minCL). At 634, data windows associated with substantially identical CL statistics, such as within a specified tolerance, may be identified. For example, a lower bound (LB) and an upper bound (UB) of maxCL may respectively be determined using a central tendency μ (e.g., an average) and a standard deviation σ of all or a portion of the maxCL computed from the data windows. In an example, LB=μ−c1*σ and UB=μ+c2*σ, where c1 and c2 are constants. Those maxCL falling within the range of (LB, UB) may be deemed substantially identical, and a relative count such as a percentage of the substantially identical maxCL may be determined as a repetitiveness indicator, which is used for detecting the cardiac arrhythmia such as atrial fibrillation (AF).

In another example, at 632 the beat patterns may include ascending CL sequences of consecutive cardiac cycles progressively increasing by at least a specified step size $\delta_1$ and descending CL sequences of consecutive cardiac cycles progressively decreasing by at least a specified step size $\delta_2$. As discussed previously with reference to FIG. 3B and Table 1, the ascending or descending CL sequences may include various beat patterns characterized by consecutive CL shortening or lengthening. The CL sequence may be transformed to a symbolic sequence comprising one or more of "S", "L", and "I" symbols that represent consecutive CL shortening or lengthening. In particular, the symbol "L" denotes CL lengthening if ΔCLi is positive and ΔCLi>$\delta_1$, the symbol "S" denotes CL shortening if ΔCLi is negative and ΔCLi<$\delta_2$, and the symbol "I" denotes identical CL if $\delta_2$<ΔCLi<$\delta_1$.

Various beat patterns may be identified from the symbolic sequence. For example, an ascending sequence of three consecutive cardiac cycles with cycle lengths CL1<CL2<CL3 may be represented by an "LL" sequence or a "+2" pattern indicating CL2 longer than the previous CL1 by at least $\delta_1$, and CL3 longer than the previous CL2 by at least $\delta_1$. In another example, a descending sequence of three consecutive cardiac cycles with cycle lengths CL1>CL2>CL3 may be represented by an "SS" sequence or a "−2" pattern indicating CL2 shorter than the previous CL1 by at least $\delta_2$, and CL3 shorter than the previous CL2 by at least $\delta_2$. The beat patterns may additionally include an identical CL sequence of two or more consecutive cardiac cycles with substantially identical cycle length, represented by an "I" sequence or a "0" pattern. Then at 634, occurrences of various beat patterns may be identified from a sequence of HRs or CLs measured from the physiological signal. A first count (N1) of ascending CL sequences and a second count (N2) of descending CL sequences may be used to determine one or more composite measures including an accumulative observed count (R), an expected count (E), and a standard deviation (SD) of counts of the ascending and descending CL sequences. A repetitiveness indicator may be computed using the composite measures O, E and SD, such as the Z statistic according to Equations (1) and (2).

At 640, a cardiac arrhythmia such as atrial fibrillation (AF) may be detected using at least the repetitiveness indicator of the beat pattern. In an example, an AF episode is detected when the percentage of the computed cycle length statistics falls below an AF threshold, such as approximately 50%. In another example, an AF episode is detected if the Z statistic as computed using Equations (1) and (2) falls below an AF threshold.

In various examples, detection of AF at 640 may additionally include an initial AF detection such as based on the stability of the HR or CL. The arrhythmia detection based on the beat pattern and repetitiveness indicator at steps 632 and 634 may affirm, reject, or modify the initial AF detection. In some examples, the repetitiveness indicator may be used to distinguish an AF episode from an unstable and organized rhythm. Examples of AF detection and discrimination between AF and unstable but organized rhythms are discussed below, such as with reference to FIG. 7.

At 650, a therapy may be delivered to the patient in response to the detection of the cardiac arrhythmia. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy may be modified to treat the detected arrhythmia, such as adjust a stimulation parameter or drug dosage. The detection of the AF, optionally along with other information such as the beat patterns and repetitiveness indicator, may be output to a system user or a process. In an example, a human-perceptible presentation or alerts about the detected arrhythmias may be generated and presented to a clinician or the patient as via the user interface 250.

Figure 7:
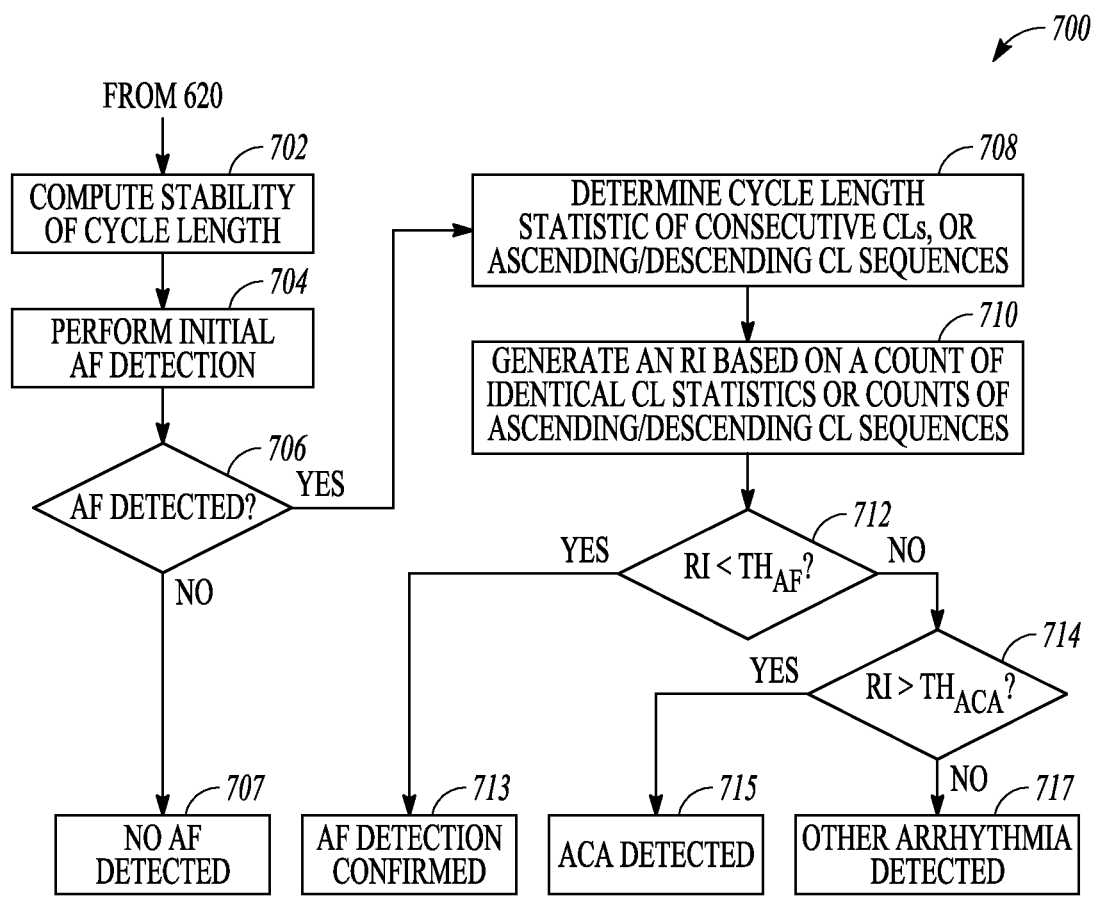
FIG. 7 illustrates generally an example of a method for detecting AF and discriminating AF from unstable and organized rhythms.

FIG. 7 illustrates generally an example of a method 700 for detecting atrial fibrillation and discriminating AF from unstable and organized rhythms. The method 700 may be an embodiment of portions of steps 630 and 640 of the method 600. In an example, the method 700 may be implemented in and executed by the arrhythmia detection system 200 in FIG. 2.

At 702, cycle length stability or heart rate stability may be computed. The stability may include difference, variance, standard deviation, or other higher-order statistics that characterize the variability of the cycle lengths or heart rates. In an example, the stability may be derived from Lorenz plot (LP) of the HRs or CLs. The LP-based stability measures may include geometric indices generated from the LP of the CLs or HRs, such as maximal length of the LP shape, maximal width of the LP shape, or a density or spreadness measure of the LP scatterplots, among others.

At 704, an initial AF detection may be performed using the CL stability. The stability-based detection may be sensitive but less specific to AF. In an example, an AF is detected if the CL variability exceeds a specified threshold.

In an example, the HRs or CLs may be classified into one of a plurality of beat classes including a stable beat class, an unstable beat class, and a random beat class. The stability may be computed as a relative quantity using the beat counts of the stable beats, the unstable beats, or the random beats. An AF is detected at 704 if the relative quantity satisfies a specified condition, such as those disclosed in the commonly assigned Mahajan et al. U.S. Patent Application 20160220139, entitled "PHYSIOLOGIC EVENT DETECTION AND DATA STORAGE," filed on Jan. 27, 2016, which is hereby incorporated by reference in its entirety, including its disclosure of beats classes and AF detection using at least the beat classes. In another example, the stability may be based on a HR or CL distribution such as a HR histogram or a CL histogram. The HR histogram or CL histogram may include percentages of the heart beats during a specified time period that fall within each of a plurality of heart rate bins. Each heart rate bin defines a range of HRs or CLs. The indicator may include a mode of the HR or CL, such as a histogram bin (or a representative heart rate value of that histogram bin) that includes the most heart beats with corresponding HRs or CLs falling within that histogram bin. The indicator may alternatively or additionally include a heart rate density index (HRDI), which may be calculated as a percentage of the heart beats falling within the histogram bin including the mode of the heart rates. The initial AF detection may be based on the mode of the heart rate or the HRDI each satisfying a specified condition, such as those disclosed in the commonly assigned Mahajan et al. U.S. patent application Ser. No. 15/082,440, entitled "ATRIAL FIBRILLATION DETECTION," filed May 28, 2016, which is hereby incorporated by reference in its entirety, including its disclosure of the HRDI and the AF detection using at least the HRDI.

If an AF is deemed detected at 706, then a beat pattern and repetitiveness-based detection method may be used to confirm, reject, or modify the initial AF detection. At 708, beat patterns such as cycle length statistics of consecutive cycle lengths, or ascending and descending CL sequences, may be determined, as previously discussed at step 632 of the method 600. At 710, a repetitiveness indicator may be generated. The RI may indicate a degree of randomness of the CLs or HRs. The RI may be computed based on a count of identical CL statistics, or based on counts of ascending or descending CL sequences, as previously discussed at step 634 of the method 600.

At 712, the repetitiveness indicator may be compared to an AF threshold. If the repetitiveness indicator falls below an AF threshold, then the AF detection is confirmed at 713. If the repetitiveness indicator exceeds the AF threshold, the underlying rhythm may be characterized by unstable cardiac cycle length but substantially organized rhythms, such as rhythms with various degrees of atrio-ventricular conduction abnormalities (ACAs), or premature atrial contractions (PACs). At 714, the repetitiveness indicator may be compared to a specified ACA threshold. If the repetitiveness indicator exceeds the ACA threshold, an ACA rhythm such as Wenckebach rhythm may be detected at 715. Otherwise, the underlying rhythm may be detected at 717 as other types of arrhythmias, which may further be classified using other timing or morphological based rhythm classification method. The detection results, including the absence or presence of AF episodes or ACA rhythms or other cardiac rhythms, may be presented to a system user, or to trigger the delivery or withholding of AF therapy.

Figure 8:
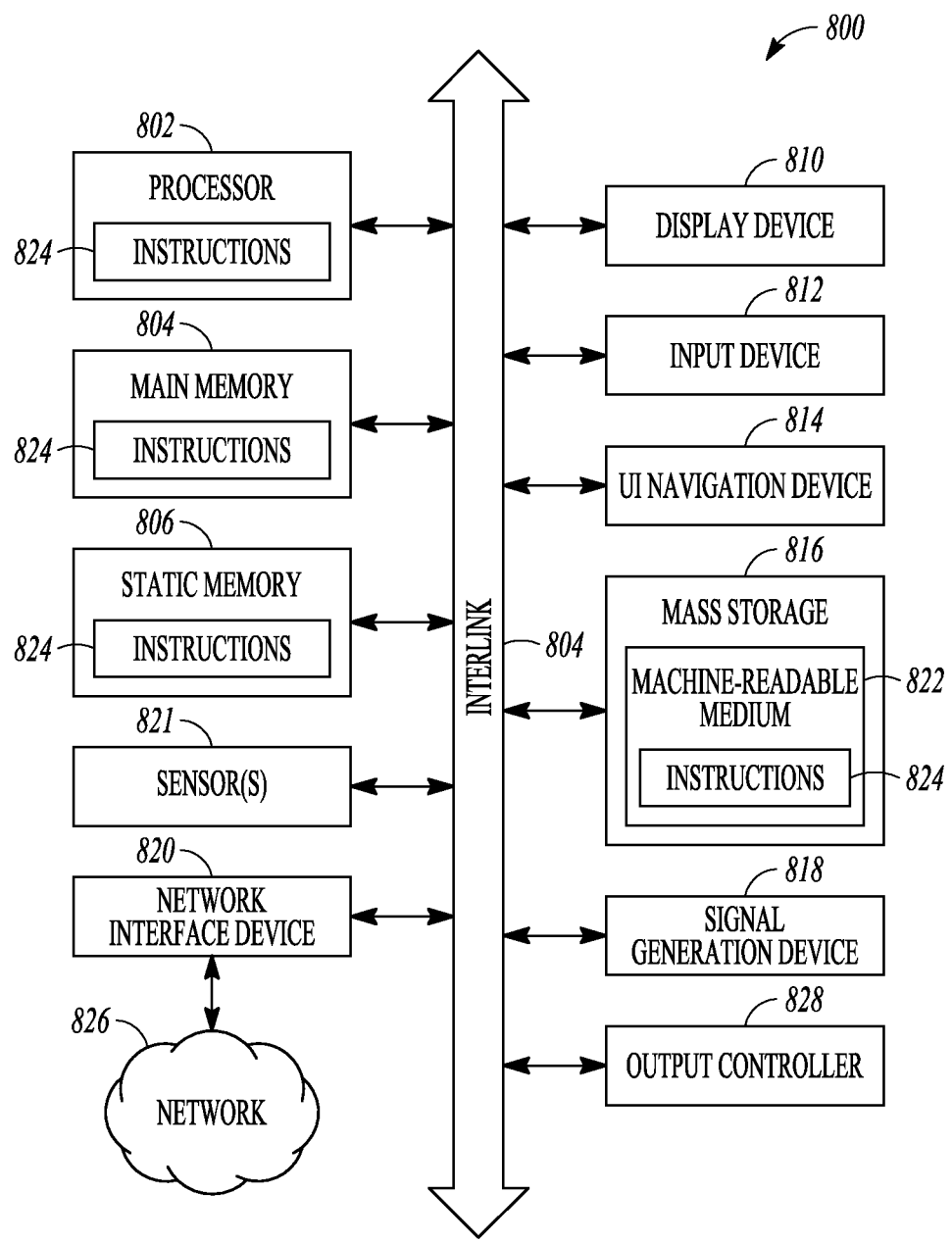
FIG. 8 illustrates generally a block diagram of an example machine upon which any one or more of the techniques (e.g., methodologies) discussed herein may perform.

FIG. 8 illustrates generally a block diagram of an example machine 800 upon which any one or more of the techniques (e.g., methodologies) discussed herein may perform. Portions of this description may apply to the computing framework of various portions of the LCP device, the IMD, or the external programmer.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensor. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine readable media.

While the machine readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

The above detailed description includes references to the accompanying drawings, which form a part of the detailed description. The drawings show, by way of illustration, specific embodiments in which the disclosure may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the disclosure should be determined with reference to the appended claims, along with the full scope of equivalents to which such claims are entitled.

What is claimed is:

1. A system for detecting cardiac arrhythmia, comprising:
   a heartbeat processor configured to:
      determine cardiac cycle lengths (CLs) from a physiological signal sensed from a subject over a window;
      identify a plurality of beat patterns each including a cycle length statistic of consecutive CLs;
      generate a repetitiveness indicator of the beat pattern using cycle length statistic;
   an arrhythmia detector coupled to the heartbeat processor and configured to detect atrial fibrillation (AF) in response to the repetitiveness indicator of the beat pattern falling below a threshold or within a range; and
   an output circuit configured to output the detected AF to a user via a user interface or to a process;
   wherein the plurality of beat patterns include CL sequences of consecutive CLs, and the repetitiveness indicator includes at least one of:
      a first count of CL sequences having substantially identical maximum CLs;
      a second count of CL sequences having substantially identical minimum CLs;
      a first count of ascending CL sequences each having two or more consecutive cardiac cycles progressively increasing by a first step size; or
      a second count of descending CL sequences each having two or more consecutive cardiac cycles progressively decreasing by a second step size.

2. The system of claim 1, comprising a therapy circuit configured to generate and deliver an AF therapy in response to the detection of AF.

3. The system of claim 1, wherein:
   the cycle length statistic includes a maximum cycle length or a minimum cycle length each computed from a CL sequence of consecutive cardiac cycles, the CL sequence having a specified number of cardiac cycles or a specified time duration;
   the repetitiveness indicator includes the first count of CL sequences having substantially identical maximum cycle length, or the second count of CL sequences having substantially identical minimum cycle length; and
   the arrhythmia detector is configured to detect the AF when the first or second count falls below a threshold.

4. The system of claim 1, wherein the beat patterns include the ascending CL sequence of two or more consecutive cardiac cycles progressively increasing by at least a specified step size, and the descending CL sequence of two or more consecutive cardiac cycles progressively decreasing by at least a specified step size;
   wherein the heartbeat processor is configured to generate the repetitiveness indicator using the first count of ascending CL sequences and the second count of descending CL sequences from the determined cardiac cycles; and
   wherein the arrhythmia detector is configured to detect the AF when the generated repetitiveness indicator falls below an AF threshold.

5. The system of claim 4, wherein the beat patterns further include an identical CL sequence of two or more consecutive cardiac cycles of substantially identical CL, and wherein the heartbeat processor is configured to generate the repetitiveness indicator further using a third count of identical CL sequences.

6. The system of claim 4, wherein the heartbeat processor is configured to generate the repetitiveness indicator using (1) an accumulative observed count including the first count of ascending CL sequences and the second count of descending CL sequences, (2) an expected count computed using the first and second counts, and (3) a standard deviation of counts of the ascending and descending CL sequences.

7. The system of claim 1, wherein the arrhythmia detector is further configured to detect atrioventricular conduction abnormality (ACA) when the repetitiveness indicator exceeds an ACA threshold.

8. The system of claim 1, further comprising an ambulatory device that includes at least a portion of one or more of the sensor circuit, the heartbeat processor, or the arrhythmia detector.

9. The system of claim 8, wherein the ambulatory device includes an implantable or wearable device.

10. The system of claim 1, wherein:
    the heartbeat processor is further configured to compute a stability of the CLs; and
    the arrhythmia detector is configured to detect the AF further based on the stability of the CLs and the repetitiveness indicator of the beat pattern.

11. A method for detecting cardiac arrhythmia, the method comprising:
    sensing a physiological signal;
    determining cardiac cycle lengths (CLs) from the sensed physiological signal over a window;
    identifying a plurality of beat patterns each including a cycle length statistic of consecutive CLs;
    generating a repetitiveness indicator of the beat pattern using the cycle length statistic;
    detecting atrial fibrillation (AF) in response to the repetitiveness indicator of the beat pattern falling below a threshold or within a range; and
    outputting the detected AF to a user via a user interface or to a process,
    wherein the plurality of beat patterns include CL sequences of consecutive CLs, and the repetitiveness indicator includes at least one of:
       a first count of CL sequences having substantially identical maximum CLs;
       a second count of CL sequences having substantially identical minimum CLs;
       a first count of ascending CL sequences each having two or more consecutive cardiac cycles progressively increasing by a first step size; or
       a second count of descending CL sequences each having two or more consecutive cardiac cycles progressively decreasing by a second step size.

12. The method of claim 11, comprising generating and delivering an AF therapy in response to the detection of AF.

13. The method of claim 11, wherein:
the cycle length statistic includes a maximum cycle length or a minimum cycle length each computed from a CL sequence of consecutive cardiac cycles, the CL sequence having a specified number of cardiac cycles or a specified time duration; and
the repetitiveness indicator includes the first count of CL sequences having substantially identical maximum cycle length, or the second count of CL sequences having substantially identical minimum cycle length;
wherein the detection of AF includes detecting AF when the first or second count falls below a threshold.

14. The method of claim 11, wherein the beat patterns include the ascending CL sequence of two or more consecutive cardiac cycles progressively increasing by at least the specified step size, and the descending CL sequence of two or more consecutive cardiac cycles progressively decreasing by at least the specified step size;
wherein the repetitiveness indicator is generated using the first count of ascending CL sequences and the second count of descending CL sequences from the determined cardiac cycles; and
wherein detecting AF includes detecting AF when the generated repetitiveness indicator falls below an AF threshold.

15. The method of claim 14, wherein the beat patterns further include an identical CL sequence of two or more consecutive cardiac cycles of substantially identical CL, and wherein determining the repetitiveness indicator further includes using a third count of identical CL sequences.

16. The method of claim 11, further comprising detecting an atrioventricular conduction abnormality (ACA) when the repetitiveness indicator exceeds an ACA threshold.

17. The method of claim 11, further comprising computing a stability of the CLs, wherein the detection of AF further includes detecting AF based on the stability of the CLs and the repetitiveness indicator of the beat pattern.

18. A system for detecting cardiac arrhythmia, comprising:
a heartbeat processor configured to:
determine cardiac cycle lengths (CLs) from a physiological signal sensed from a subject;
determine a first count of ascending CL sequences each comprising two or more consecutive cardiac cycles progressively increasing by at least a specified step size;
determine a second count of descending CL sequences each comprising two or more consecutive cardiac cycles progressively decreasing by at least a specified step size; and
generate a randomness indicator of the determined CLs using the first and second counts;
an arrhythmia detector configured to detect atrial fibrillation (AF) using the generated randomness indication; and
an output circuit configured to output the detected AF to a user via a user interface or to a process.

19. The system of claim 18, wherein the heartbeat processor is configured to generate the randomness indicator including:
determine an accumulative observed count and an expected count using the determined first and second counts; and
generate the randomness indicator based on a difference between the accumulative observed count and the expected count.

20. The system of claim 18, wherein the heartbeat processor is further configured to:
determine a standard deviation of counts of the ascending and descending CL sequences; and
generate the randomness indicator using a ratio of the difference between the accumulative observed count and the expected count to the determined standard deviation.

* * * * *